(12) United States Patent
Samakar

(10) Patent No.: US 11,786,401 B2
(45) Date of Patent: Oct. 17, 2023

(54) PERISTALTIC MICROPUMP ASSEMBLIES AND ASSOCIATED DEVICES, SYSTEMS, AND METHODS

(71) Applicant: Verily Life Sciences LLC, South San Francisco, CA (US)

(72) Inventor: Amir Samakar, Fremont, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 483 days.

(21) Appl. No.: 16/820,293

(22) Filed: Mar. 16, 2020

(65) Prior Publication Data

US 2020/0297536 A1 Sep. 24, 2020

Related U.S. Application Data

(60) Provisional application No. 62/819,902, filed on Mar. 18, 2019.

(51) Int. Cl.
*A61F 9/007* (2006.01)
*F04B 45/08* (2006.01)
(Continued)

(52) U.S. Cl.
CPC .......... *A61F 9/00781* (2013.01); *F04B 17/03* (2013.01); *F04B 45/08* (2013.01);
(Continued)

(58) Field of Classification Search
CPC .......... F04B 17/03; F04B 45/08; F04B 49/06; A61F 9/00781; A61F 2250/0001; H02J 7/02
See application file for complete search history.

(56) References Cited

U.S. PATENT DOCUMENTS 2,920,578 A 1/1960 Schaurte
3,922,119 A * 11/1975 Rosenquist ......... F04B 43/0054
417/474

(Continued)

FOREIGN PATENT DOCUMENTS

FR 2200907 * 8/1974
WO 2007106557 A2 9/2007
(Continued)

OTHER PUBLICATIONS

English translation of FR2200907 obtained Jun. 23, 2022 (Year: 2022).*

(Continued)

*Primary Examiner* — Connor J Tremarche
(74) *Attorney, Agent, or Firm* — Haynes and Boone, LLP

(57) ABSTRACT

Peristaltic micropump assemblies configured to pump fluid from a patient and/or deliver pharmaceutical agents to the patient are provided. In some embodiments, a micropump assembly can include a rotor configured to rotate about an axis and comprising a compressing member configured to rotate along a circumference, and a fluid chamber positioned at least partially around the circumference. The fluid chamber includes a round outer ring and a membrane attached to the outer ring and opposing an inner face of the outer ring. The compressing member is configured to compress the fluid chamber and move a fluid through the fluid chamber. The assembly can fit within a housing that is sized and shaped to be implanted in the patient. For example, the micropump assembly can be inserted into the patient's ocular cavity and configured to displace fluid from the patient's eye.

15 Claims, 9 Drawing Sheets

(51) Int. Cl.
*F04B 17/03* (2006.01)
*F04B 49/06* (2006.01)
*H02J 50/10* (2016.01)
*H02J 7/02* (2016.01)

(52) U.S. Cl.
CPC ...... *F04B 49/06* (2013.01); *A61F 2250/0001* (2013.01); *H02J 7/02* (2013.01); *H02J 50/10* (2016.02)

(56) References Cited

U.S. PATENT DOCUMENTS

| | | | |
|---|---|---|---|
| 4,545,745 A | 10/1985 | Barreca | |
| 5,380,173 A | 1/1995 | Hellstrom | |
| 5,470,211 A | 11/1995 | Knott et al. | |
| 6,099,495 A * | 8/2000 | Kinghorn | A61M 5/14276 604/93.01 |
| 6,296,460 B1 | 10/2001 | Smith | |
| 9,618,129 B2 | 4/2017 | Block, III et al. | |
| 2002/0001530 A1 | 1/2002 | Doi et al. | |
| 2004/0111050 A1* | 6/2004 | Smedley | A61F 9/00781 604/9 |
| 2005/0047925 A1* | 3/2005 | Davis | F04B 43/1253 417/53 |
| 2008/0131300 A1 | 6/2008 | Junod et al. | |
| 2009/0012448 A1* | 1/2009 | Childers | A61M 1/14 604/29 |
| 2009/0053085 A1 | 2/2009 | Thompson et al. | |
| 2013/0261530 A1 | 10/2013 | Yalamanchili | |
| 2013/0287613 A1* | 10/2013 | Gould | C12M 23/16 417/476 |
| 2014/0081202 A1* | 3/2014 | Tsoukalis | A61M 5/142 604/153 |
| 2014/0194834 A1 | 7/2014 | Passaglia | |
| 2018/0149152 A1 | 5/2018 | Asai et al. | |

FOREIGN PATENT DOCUMENTS

| | | |
|---|---|---|
| WO | 2011006921 A1 | 1/2011 |
| WO | 2012048261 A2 | 4/2012 |
| WO | 2018/046078 A1 | 3/2018 |

OTHER PUBLICATIONS

International Search Report and Written Opinion—PCT/US2020/023191, dated May 28, 2020. (7 pgs).

* cited by examiner

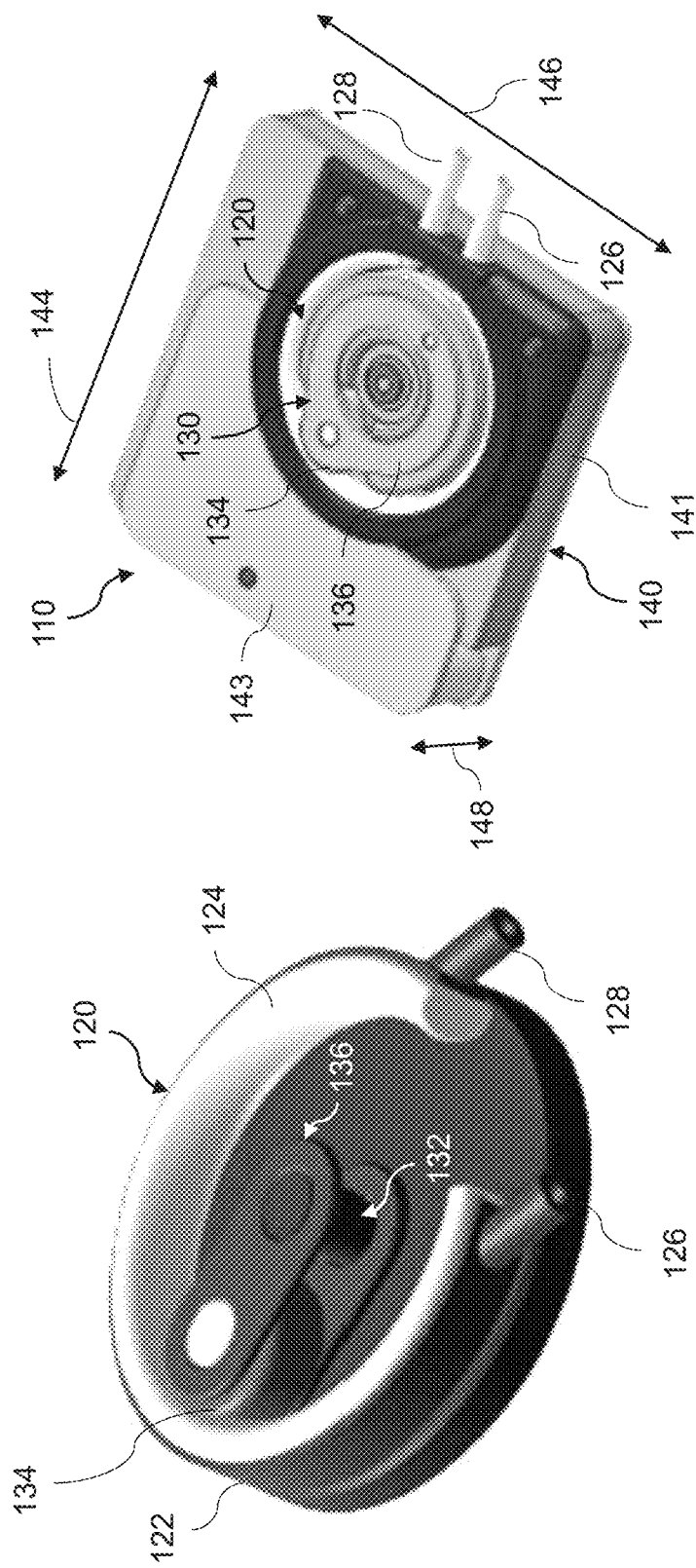

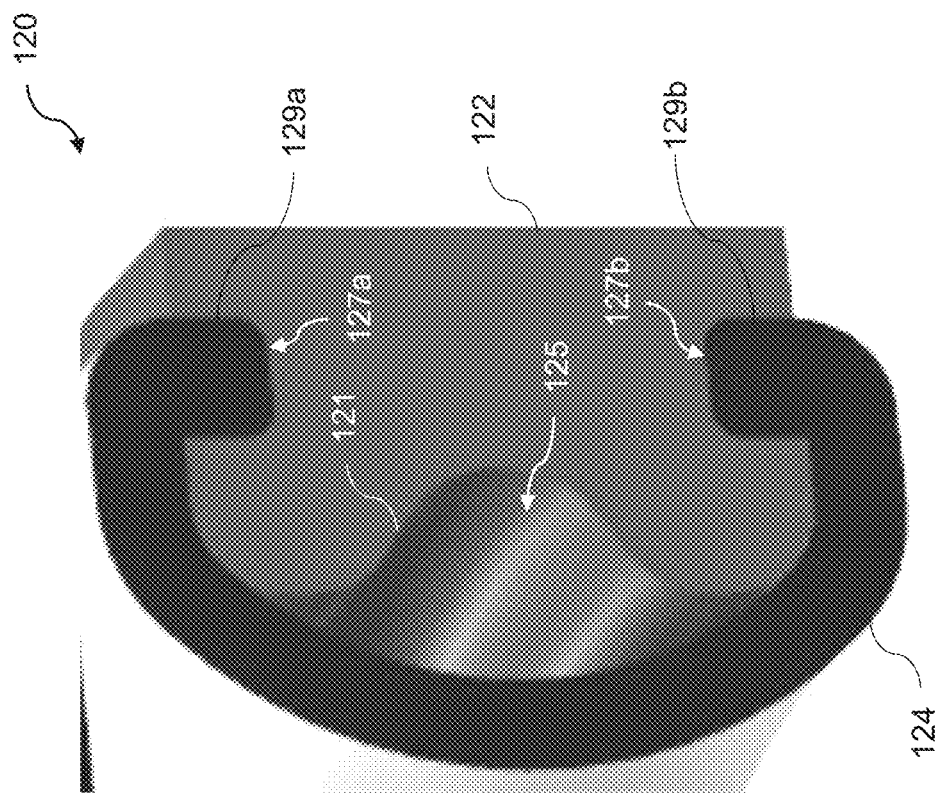

PERISTALTIC MICROPUMP ASSEMBLIES AND ASSOCIATED DEVICES, SYSTEMS, AND METHODS

CROSS-REFERENCE TO RELATED APPLICATIONS

The present application claims priority to and the benefit of U.S. Provisional Patent Application No. 62/819,902, filed Mar. 18, 2019, the entirety of which is incorporated by reference in its entirety.

TECHNICAL FIELD

The present disclosure relates generally to devices and methods for pumping fluids from a patient and/or delivering pharmaceutical agents to a patient, including peristaltic pump assemblies implantable in a patient for relieving intraocular pressure.

BACKGROUND

Intraocular pressure (IOP) quantifies the pressure of the aqueous humor inside the eye. Many individuals suffer from disorders, such as glaucoma, that cause chronic heightened IOP. Over time, heightened IOP can cause damage to the optical nerve of the eye, leading to loss of vision. Presently, treatment of glaucoma mainly involves periodically administering pharmaceutical agents to the eye to decrease TOP. These drugs can be delivered by, for example, injection or eye drops. However, the effectiveness of pharmaceuticals can vary greatly from patient-to-patient. Furthermore, effective treatment of glaucoma requires adherence to rigid dosage schedules that can be difficult to follow for some patients.

Another way TOP can be reduced is by removing some of the fluid from inside the patient's eye. However, current devices are not suitable or practical for therapeutic use. For example, current devices do not simultaneously satisfy the desire for small size, low power, and a lifetime of many years before failure. Thus, there remains a need for wearable fluid displacement devices that meet requirements for safety and reliability while being as cost-effective as possible.

SUMMARY

The present disclosure advantageously describes micropump assemblies configured to pump fluid from a patient and/or deliver pharmaceutical agents to the patient. In some embodiments, a micropump assembly can include a compressing member and a round fluid chamber comprising an outer portion and a flexible membrane coupled to the outer portion. The compressing member is controlled by a motor to rotate along a circumference to compress the fluid chamber in a circular motion, thereby pumping a fluid through the fluid chamber. The assembly can fit within a housing that is sized and shaped to be implanted in the patient. For example, the micropump assembly can be inserted into the patient's ocular cavity and configured to displace fluid from the patient's eye.

In one embodiment of the present disclosure, a pump assembly includes a rotor configured to rotate about an axis and comprising a compressing member at an outer portion of the rotor such that the compressing member is configured to rotate along a circumference, and a fluid chamber positioned at least partially around the circumference, the fluid chamber comprising a round outer portion and a membrane attached to the round outer portion and opposing an inner face of the round outer portion, wherein the compressing member is configured to deform the membrane of the fluid chamber to compress the fluid chamber and move a fluid through the fluid chamber.

In one aspect, the pump assembly is implantable in a patient for relieving intraocular pressure (IOP). In some embodiments, the pump assembly further comprising an actuator configured to cause the rotor to rotate about the axis. The actuator can include an electrostatic motor. In some embodiments, the rotor comprises a gear concentric with the first axis, wherein the actuator is configured to cause the rotor to rotate about the first axis via the gear. In another aspect, the fluid chamber is positioned around the axis in a non-circular pattern. In another aspect, the round outer portion comprises a hard ring and the membrane comprises an elastomeric material. The hard ring can include a first groove on one side and a second groove on an opposing side, wherein the membrane is joined to the hard ring using the first groove and the second groove. In some embodiments, the hard ring includes at least one of a flat surface or a concave inner surface, and the membrane comprises a thin wall tube comprising a soft rubber material. According to a further aspect, the hard ring and the membrane are attached by at least one of an adhesive or a weld.

According to another embodiment of the present disclosure, a peristaltic pump implantable in a patient for relieving intraocular pressure (IOP) includes, an actuator, a drive shaft coupled to the actuator and configured to rotate about a first axis, a roller coupled to and radially extending from the drive shaft such that the actuator, via the drive shaft, is configured to rotate the roller about the first axis and along a circumference, and a fluid chamber disposed around a portion of the circumference, the fluid chamber comprising a hard outer ring and a flexible inner ring positioned over an inner surface of the outer ring, wherein the roller is configured to deform the inner ring of the fluid chamber to compress the fluid chamber and move a fluid through the fluid chamber.

In some embodiments, the outer ring comprises a first groove on one side and a second groove on an opposing side, wherein the membrane is joined to the outer ring using the first groove and the second groove, wherein the membrane comprises a first ridge portion and a second ridge portion, wherein the first ridge portion resides in the first groove, and wherein the second ridge portion resides in the second groove. In another embodiment, the drive shaft is rotatably coupled to the roller via a first ball bearing, wherein the roller comprises a second ball bearing, and wherein the roller is configured to rotate about a second axis of the ball bearing.

In yet another embodiment, the peristaltic pump further includes a gear assembly coupled to the actuator and the drive shaft, wherein the gear assembly is configured to convert a torque provided by the actuator to the drive shaft. In some embodiments, the peristaltic pump further comprises an application specific integrated circuit (ASIC) configured to activate the actuator, and a rotary encoder configured to indicate a rotational position of the roller to the ASIC, wherein the ASIC is configured to control rotation of the roller by the actuator based on the rotational position provided by the encoder.

According to another embodiment, the peristaltic pump includes a processor configured to control an output of the actuator, a battery configured to provide electrical power to the processor and the actuator, a wireless charging coil coupled to the processor and the battery, the wireless charging coil configured to receive wireless power to recharge the battery, and a housing sized and shaped to be implanted in an eye cavity of a patient, wherein the actuator, drive shaft, roller, fluid chamber, processor, battery, and wireless charging coil are coupled to and contained within the housing. In another embodiment, the fluid chamber comprises a circular section and a non-circular section, wherein the non-circular section is positioned with respect to the first axis such that a radius between the first axis and the non-circular section of the fluid chamber increases in a direction of the circumference.

According to another aspect of the present disclosure, a method for pumping a fluid from a patient's eye to relieve intraocular pressure comprises compressing, in a circular motion, a fluid chamber in fluid communication with the patient's eye using a compressing member to pump a fluid through the fluid chamber, wherein compressing the fluid chamber comprises rotating the compressing member along a circumference by activating a motor coupled to the compressing member, wherein the compressing member compresses the fluid chamber along a circumference to pump the fluid through the fluid chamber, wherein compressing the fluid chamber includes deforming a flexible inner ring against a hard outer ring.

In some embodiments, the method further includes receiving, at an application specific integrated circuit (ASIC) in communication with the motor, a signal from a rotary encoder indicating a rotational position of the compressing member, and adjusting, by the ASIC, a rotational position of the motor based on the received signal. In another embodiment, the method further includes receiving, at an application specific integrated circuit (ASIC) in communication with the motor, a signal from a pressure sensor indicating a fluid pressure, and adjusting, by the ASIC, an output of the motor based on the received signal. In yet another embodiment, the method further includes stopping the motor, and adjusting a fluid flow through the fluid chamber to a predetermined fluid flow, wherein adjusting the fluid flow comprises stopping the motor to position the compressing member at a location along a non-circular portion of the fluid chamber corresponding to the predetermined fluid flow.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 3 is a perspective view of a driver assembly and fluid chamber of a micropump assembly, according to an embodiment of the present disclosure.

FIG. 4 is a perspective view of a micropump assembly, according to an embodiment of the present disclosure.

FIG. 5 is a cross-sectional perspective view of a fluid chamber of a micropump assembly, according to an embodiment of the present disclosure.

DETAILED DESCRIPTION

Figure 1:
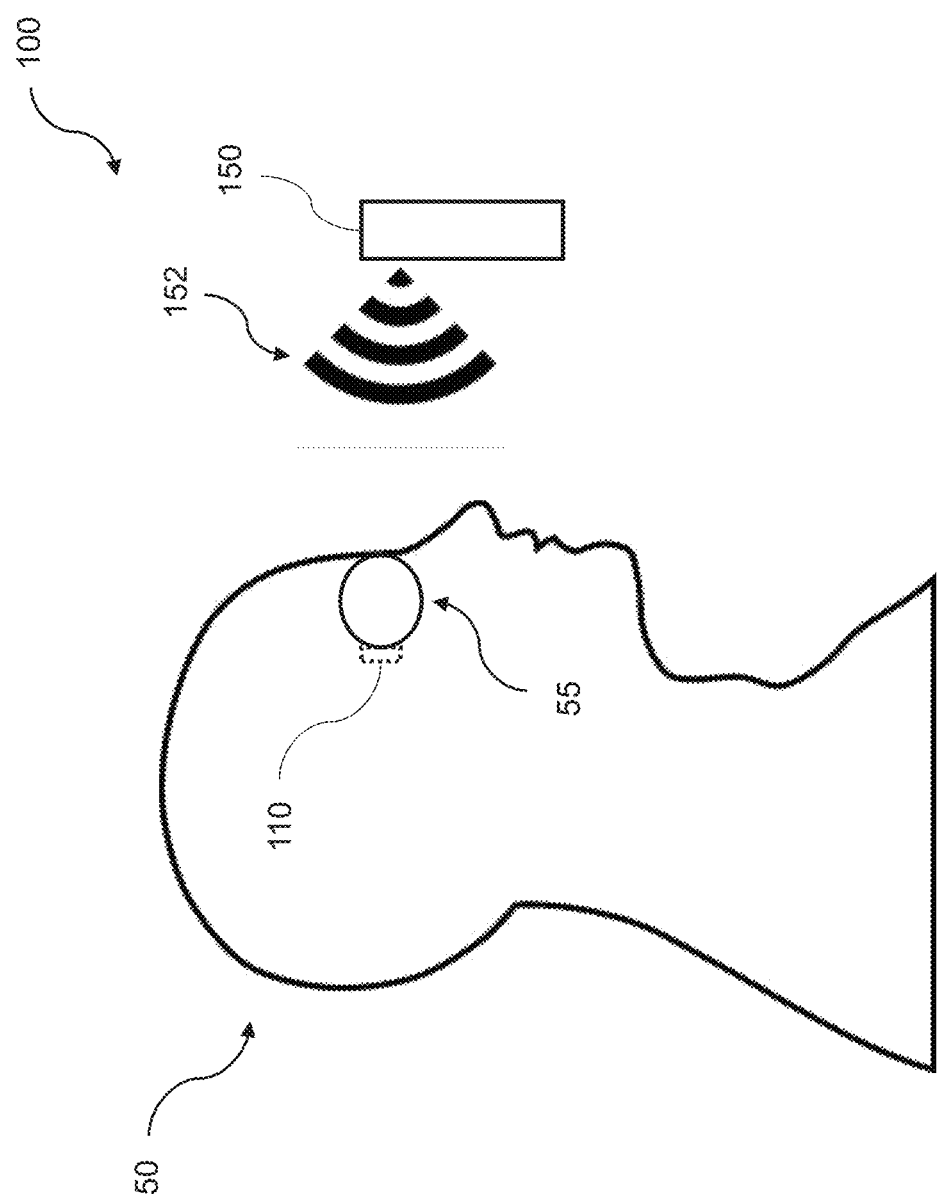
FIG. 1 is a diagrammatic view of a micropump system, according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the therapeutic devices are described in terms of eye-mountable devices configured to pump fluid (e.g., aqueous humor) from a human eye, it is understood that it is not intended to be limited to this application. The devices and systems are equally well suited to any application requiring pumping of fluids. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Presently, treatment of glaucoma mainly consists of periodically administering pharmaceutical agents to the eye to decrease TOP. These drugs can be delivered by, for example, injection or eye drops. However, the effectiveness of pharmaceuticals can greatly vary from patient-to-patient. Furthermore, effective treatment of glaucoma requires adherence to rigid dosage schedules that can be difficult to follow for some patients.

Another way to reduce TOP involves removing quantities of fluid from inside the patient's eye. However, current devices are not suitable or practical for therapeutic use. For example, devices to remove fluid from the eye need to be small enough to be implanted into the patient at a practical location, such as the patient's eye cavity. Due to the invasiveness of implanting such a device, the device should be able to operate independently for a period of time. Thus the device must be able to operate efficiently in a restricted space, and must be reliable enough to require little or no maintenance.

The present disclosure describes micropump assemblies that overcome the challenges described above. In that regard, the micropump assemblies described herein provide advantageous arrangements of components and features that allow the micropumps to reliably and efficiently pump fluid from a patient's eye while minimizing the profile of the devices such that they can be implanted and worn by patients for extended periods of time.

FIG. 1 is a diagrammatic view of a micropump system 100, according to one embodiment. The system 100 includes an eye-mountable micropump 110 coupled to an eye 55 of a patient 50, and a wireless transmission device 150 configured to wirelessly transmit electrical power 152 and/or electrical signals to the micropump 110. The micropump 110 is sized and shaped to be permanently or semi-permanently attached to the patient's eye 55. In particular, the micropump 110 is configured to be positioned within an ocular cavity proximate the eye 55. In some embodiments, the micropump 110 can be positioned at different locations with respect to the patient's eye, such as below the eye 55, above the eye 55, inside the eye 55, or inside any suitable anatomical structure that allows the micropump to pump fluid from the eye 55.

Because the micropump 110 may not be easily accessible for charging or reprogramming, the micropump 110 is configured to wirelessly receive electrical power 152 and/or electrical signals from the wireless transmission device 150. The wireless transmission device 150 includes circuitry and components to send electrical power, such as coils, transformers, power supplies, batteries, or other circuitry. Additionally, the wireless transmission device 150 can include wireless communication components to transmit and/or receive data in the form of wireless signals to/from the micropump 110. As explained further below, the micropump 110 can also include wireless electronic components for receiving electrical power and/or electrical signals form the transmission device 150. The micropump 110 can include a battery and a processing component that allow it to operate independently for a period of time (e.g., days, weeks, months) without receiving power or signals from the transmission device 150.

Figure 2:
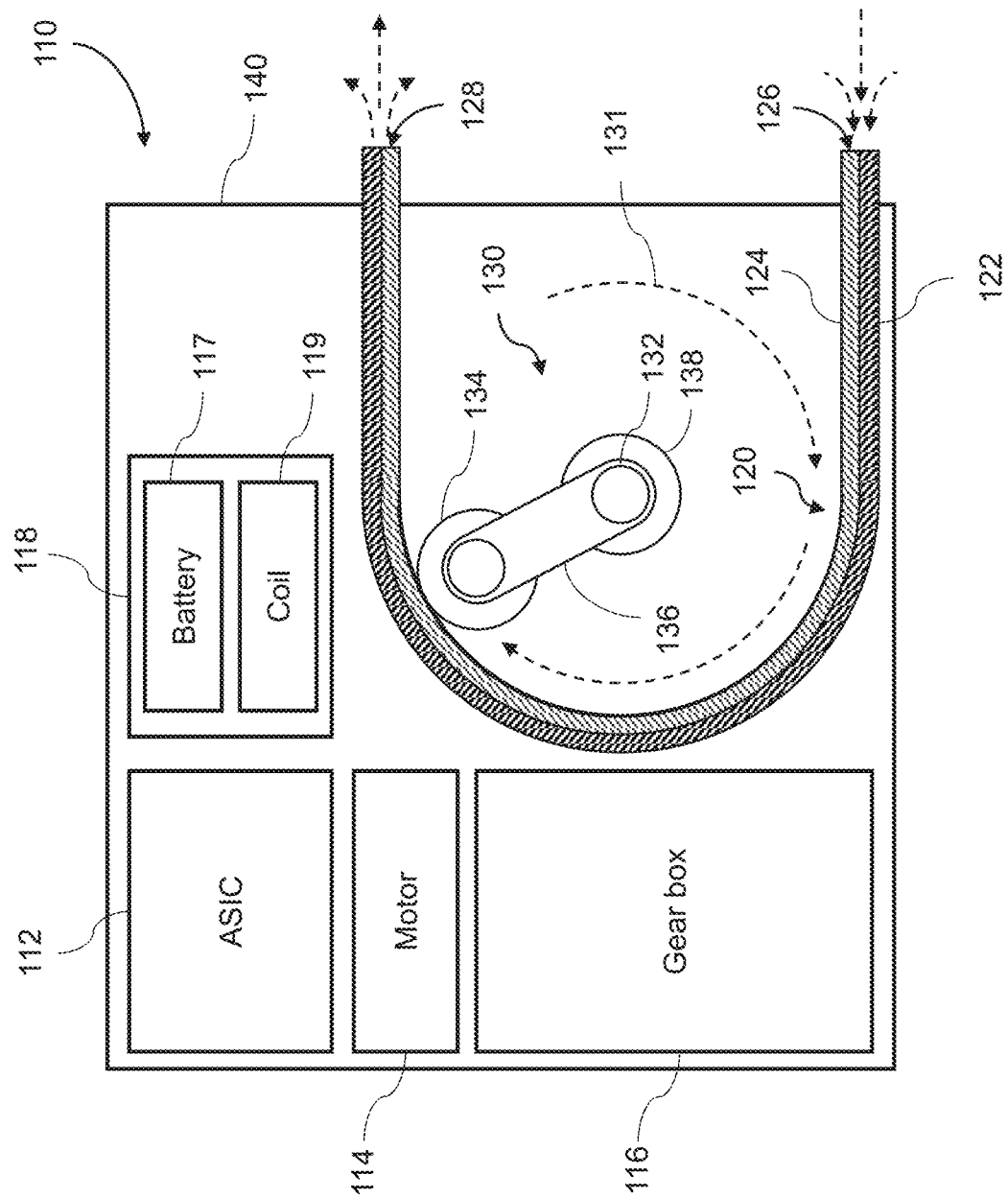
FIG. 2 is a diagrammatic schematic view of a micropump assembly, according to an embodiment of the present disclosure.

FIG. 2 is a diagrammatic schematic view of a micropump assembly 110, according to one embodiment of the present disclosure. The micropump assembly 110 includes a compressible fluid chamber 120 and a driver assembly 130 configured to compress the fluid chamber 120 to move fluid through the fluid chamber 120. The driver assembly 130 is actuated and controlled by a plurality of electronic and mechanical components, such as an application-specific integrated circuit (ASIC) 112, an actuator or motor 114, a gear box 116, and a power circuit 118. The power circuit 118 includes a battery 117, and a coil 119 configured to receive electrical power from a wireless source, such as the wireless transmission device 150 shown in FIG. 1. The power circuit 118 is configured to supply electrical power to the components of the micropump 110, including the ASIC 112, and the motor 114. The power circuit 118 separately provides electrical power to the ASIC 112 and the motor 114, in some embodiments. In other embodiments, the power circuit 118 provides electrical power to the ASIC 112, which distributes the electrical power to the other components of the micropump assembly 110, including the motor 114.

The ASIC 112 is configured to control an output of the motor 114, thereby controlling the performance (e.g., flow rate) of the micropump 110 assembly. The ASIC 112 operates according to a protocol, which comprises computer code instructions saved in a memory device of the ASIC 112. The protocol is defined by one or more parameters, such as time, number of cycles, physiological measurements, battery life, etc. Thus, the ASIC 112 is configured to control operation of the micropump assembly 110 while the assembly 110 is implanted in the patient. It will be understood that, although the ASIC 112 is shown as a single component in FIG. 2, the micropump assembly 110 may comprise a plurality of individual integrated circuits or other circuitry that is configured to carry out the functions of the assembly 110.

The power circuit 118 and/or the ASIC 112 provide electrical power to the motor 114, which is configured to activate the driver assembly 130 via the gear box 116. The gear box 116 is configured to modify or convert a torque provided by the motor 114, and apply the modified torque to the driver assembly 130. In that regard, the gear box 116 comprises one or more gears or stages of gears to increase or decrease the torque applied by the motor 114. Thus, the gear box 116 can also be appropriate referred to as a torque converter. In an exemplary embodiment, the gear box 116 is configured to increase the torque applied by the motor 114. The increased torque provided by the gear box 116 can help to overcome friction on the driver assembly 130 caused by, e.g., the roller 134 on the compressible fluid chamber 120.

In an exemplary embodiment, the motor 114 is an electrostatic motor, such as the Silmach PowerMEMS® electrostatic motor. However, other motors are also contemplated by the present disclosure, including lavet-type motors, piezoelectric motors, step motors, brushless motors, or any other suitable type of motor.

The driver assembly 130 includes a drive shaft 132 configured to rotate about a first axis and a compressing member or roller 134 rotatably coupled to the drive shaft 132 by a rotor 136. The rotor 136, which can also be referred to as a crank, couples the roller 134 to the drive shaft 132 such that the roller 134 travels about the first axis of the drive shaft 132 along a circumference 131 or circular path when the drive shaft 132 is rotated by the motor 114 via the gear box 116. The roller 134 is rotatably coupled to the rotor 136, such that the roller can rotate about a second axis while traveling along the circumference 131. As described further below, the drive shaft 132 and roller 134 can each comprise one or more ball bearings, such as the drive shaft bearing 138, to reduce friction, and therefore reduce the amount of torque required to rotate the driver assembly 130.

As the driver assembly 130 rotates the roller 134 along the circumference, the roller compresses the fluid chamber 120 in a circular motion around the circumference 131. This circular compression causes the peristaltic pumping action that moves fluid into the fluid chamber 120 through an inlet 126, through the fluid chamber 120 in the circumferential direction 131, and out the fluid chamber 120 through an outlet 128. As an example, when the micropump assembly 110 is implanted onto the patient's eye 55, the inlet 126 can be coupled the eye 55 to receive the aqueous humor, and the outlet 128 can be positioned outside the eye 55, for example, in the ocular cavity. When the micropump assembly 110 is activated, the micropump 110 draws the fluid from inside the eye 55, and expels the fluid outside of the eye 55, thereby reducing the patient's intraocular pressure (IOP).

The fluid chamber 120 can include a round outer portion, or ring 122, and a flexible membrane 124 coupled to the hard outer ring 122 and opposing an inner surface of the outer ring 122. The outer ring 122 can comprise a material that is relatively harder and/or more rigid than the flexible membrane, such as a plastic. As will be explained further below, compression of the fluid chamber 120 involves deforming the membrane 124 toward the outer ring 122 to close or restrict a channel formed between the outer ring 122 and the membrane 124. As will be understood with reference to the embodiment of FIG. 2, the outer ring 122 is not necessarily circular. For example, in FIG. 2, the outer ring 122 includes a circular arc portion and a linear portion. In that regard, the outer ring 122 is not closed, but forms a U-shape. Thus, although the term "ring" is used with respect to the outer portion or ring 122, this is in no way limiting to closed, circular shapes.

The components of the micropump assembly 110, including the driver assembly 130, fluid chamber 120, ASIC 112, motor 114, gear box 116, and power supply circuit 118 are coupled to and/or contained within a housing 140. The housing 140 is sized and shaped to be implanted into an ocular cavity of the patient 50. The housing 140 is configured to contain and protect the components of the micropump assembly 110 from physical and/or chemical damage. In some embodiments, the housing 140 provides a waterproof casing for one or more electrical components of the device, such as the ASIC 112, the power circuit 118, and the motor 114. The housing 140 may also be configured to protect one or more components from chemical damage. In some embodiments, the housing 140 is configured to protect the mechanical components, such as the gear box 116 and the driver assembly 130 from foreign material that could interfere with or inhibit the mechanical performance of the micropump 110.

FIG. 3 is a perspective view of a drive assembly and fluid chamber 120 of the micropump assembly 110, according to one embodiment. As in the embodiment shown in FIG. 2, the embodiment of FIG. 3 includes a drive shaft 132 and a roller 134 rotatably coupled to the drive shaft 132 by the rotor or crank 136. The roller 134 is configured to travel in a circular motion about a first axis of the drive shaft 132. The fluid chamber 120 includes a hard outer ring 122, and a flexible membrane 124 opposing an inner face or surface of the outer ring 122. An inlet 126 and an outlet 128 of the fluid chamber 120 are integrally formed with the outer ring 122 and are configured to direct ingress and egress of fluid through the fluid chamber 120. However, in other embodiments, the inlet 126 and/or outlet 128 are not integrally formed with the outer ring 122. For example, the inlet 126 and/or outlet 128 can be formed of the membrane 124, or formed of both the membrane 124 and the outer ring 122. In other embodiments the inlet 126 and/or outlet 128 can comprise physically separate components that are attached to the outer ring 122 and/or the membrane 124. As described above, as the roller 134 rotates about the circumference 131, the membrane 124 is deformed or pressed against the outer ring 122 to move fluid through the fluid chamber 120 in a peristaltic motion toward the outlet 128. To reduce friction, the roller 134 is also configured to rotate or spin in a planetary motion about a second axis and around the first axis.

FIG. 4 is a perspective view of a micropump assembly 110, according to an embodiment of the present disclosure. Similar to the assembly 110 shown in the FIG. 2, FIG. 4 shows a driver assembly 130 and a fluid chamber 120 contained within a housing 140. In contrast to the embodiments shown in FIGS. 2 and 3, the rotor or crank 136 shown in FIG. 4 has a circular shape and is positioned around the drive shaft 132. The circular rotor 136 couples the roller 134 to the drive shaft 132 such that the roller 134 travels around the first axis along a circumference.

The assembly 110 includes a housing 140 that houses the components of the assembly 110, including the driver assembly 130 and the fluid chamber 120. Other components are also positioned within the housing, such as the ASIC 112, motor 114, gear box 116, power circuit 118, or any other suitable components. The housing 140 shown in FIG. 4 includes multiple pieces, including a first piece 141 and a second piece 143. The second piece 143 may act as a cover for one or more components such as the gear box 116 and the motor 114. The housing 140 is configured to contain the components of the assembly 110 within a space small enough to be implanted into the patient. In that regard, the assembly 110 comprises a length 144, a width 146, and a height 148. In an exemplary embodiment, the length 144 is about 9 mm, the width 146 is about 9 mm, and the height 148 is about 2 mm. However, the dimensions can be modified as appropriate for the application. For example, the length 144, width 146, and/or height 148 can range from less than 1 mm to more than 30 mm. In an exemplary embodiment, the height 148 can range between 1 mm and 5 mm. The length and width can vary between 5 mm and 30 mm. It will be understood that these dimensions are merely exemplary and can be modified as suitable for a particular application.

FIG. 5 is a perspective cross-sectional view of the fluid chamber 120 of the assembly 110. The fluid chamber 120 includes an outer ring 122, and a flexible membrane 124 coupled to the outer ring 122 to define a fluid channel 125. The flexible membrane 124 comprises an elastomeric material such as silicone, while the outer ring 122 comprises a relatively harder material, such as a plastic. In some embodiments, the outer ring 122 can comprise one or more metallic materials, such as stainless steel and/or titanium, one or more plastic materials such as polyetheretherketone (PEEK) and/or polytetrafluoroethylene (PTFE), and rubber, such as a rubber having a Shore D hardness, or any other suitable material. The flexible membrane 124 or inner ring can comprise a relatively soft, flexible material, such as a soft rubber, silicone, polyethylene terephthalate (PET), PTFE, or any other suitable material. The membrane 124 is positioned over, or opposing, an inner surface 121 of the outer ring 122. The inner surface 121 comprises a valley that partially defines the fluid channel 125. The membrane 124 is attached to the outer ring 122 at a first groove 127a on a top side of the outer ring 122, and a second groove 127b on an opposing bottom side of the outer ring 122. A first ridge 129a of the membrane 124 is positioned within the first groove 127a, and a second ridge 129b of the membrane 124 is positioned within the second groove 127b. The first and second ridges 129a, 129b can be attached to the outer ring 122 by any suitable method, including a weld, thermal bond, adhesive, or a mechanical fit (e.g., interference fit). It will be understood that, in some embodiments, the first and second ridges 129a, 129b, are formed of opposing edges of a rectangular membrane.

As explained above, the outer ring 122 may comprise a material that is relatively harder and/or more rigid than the membrane 124. Accordingly, while the membrane 124 is configured to be deformed by the roller 134, the outer ring 122 may be configured to retain its shape, even with applied pressure from the roller 134. In a relaxed or undeformed state, the membrane 124 spans across the curved inner surface 121 of the outer ring 122 such that a space exists in the fluid channel 125 for a fluid to pass through. When the roller 134 passes over the membrane 124, the membrane 124 is deformed toward the inner surface 121 of the outer ring 122 to reduce or close the space in the fluid channel 125. The membrane 124 is thus deformed in a circular fashion around the circumference to create a peristaltic pumping action that moves a fluid through fluid chamber 120 toward the outlet 128.

The fluid chamber 120 described above exhibits certain advantages to existing fluid chambers. For example, the coupling of the membrane 124 to the hard outer ring 122 can reduce the stress applied to the fluid chamber 120 when compressed by the driver assembly 130. In that regard, as opposed to flexible tubes that are compressed by collapsing one side of the tube toward the other side of the tube, compressing the fluid chamber 120 shown in FIG. 5 is accomplished by deforming the flexible membrane against the relatively hard or rigid outer ring 122. Thus, when the membrane 124 is relaxed, the channel 125 of the fluid chamber 120 between the membrane and the outer ring 122 is relatively unrestricted. Compressing the membrane 124 against the outer ring 122 can be achieved with relatively little stress to any given portion of the flexible membrane 124. Furthermore, because the outer ring 122 provides the structural integrity to define the channel 125, the flexible membrane can be formed of a soft elastomeric material that can be more easily compressed. Furthermore, the smooth, round surface 121 can also reduce the amount of stress on the membrane 124 during compression. Thus, the fluid chamber 120 can be compressed with less resistance than what would be required with flexible tubing. Furthermore, because the membrane 124 undergoes relatively little stress, the durability and lifespan of the fluid chamber 120 can be increased.

Figure 7:
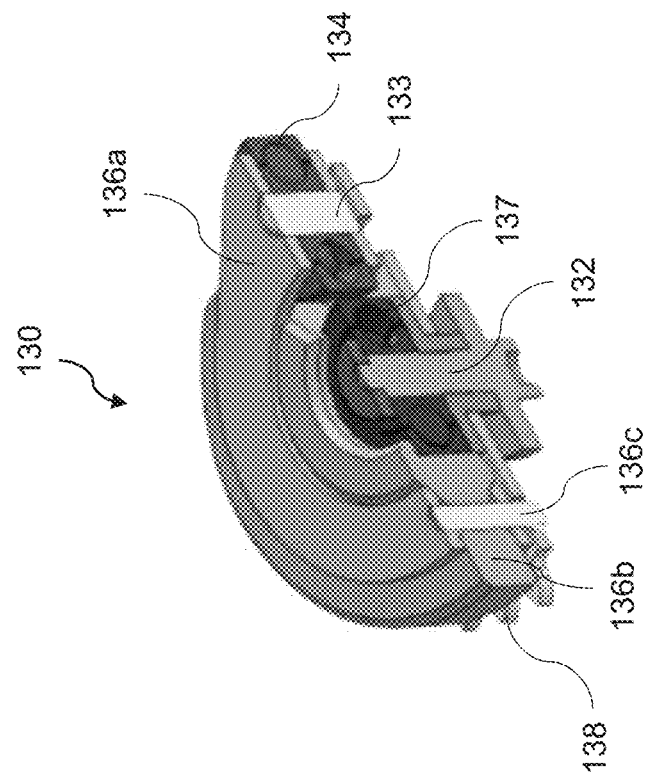
FIG. 7 is a cross-sectional perspective view of the driver assembly of FIG. 6, according to an embodiment of the present disclosure.
Figure 6:
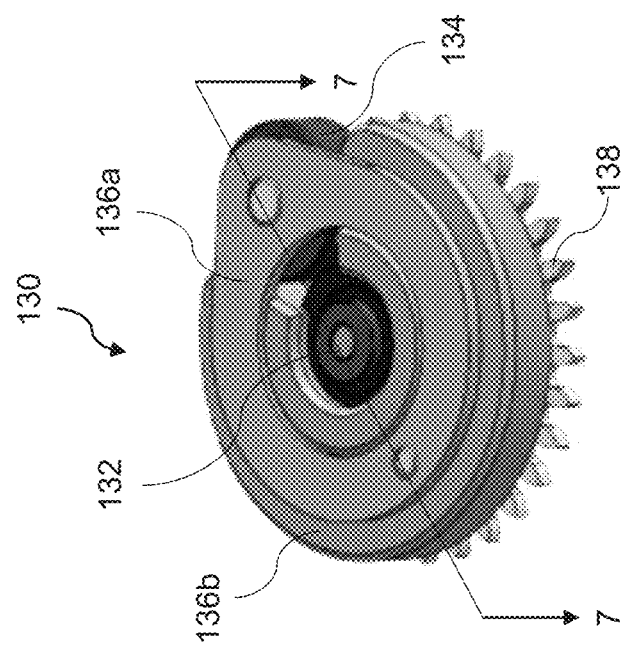
FIG. 6 is a perspective view of a driver assembly of a micropump assembly, according to an embodiment of the present disclosure.

FIGS. 6 and 7 depict a driver assembly 130 of the micropump assembly 110 shown in FIG. 4, according to one embodiment of the present disclosure. In particular, FIG. 6 is a perspective view of the driver assembly 130, and FIG. 7 is a perspective cross-sectional view of the driver assembly 130 taken along the line 7-7. As in FIG. 4, the driver assembly 130 includes a drive shaft 132 and a rotor or crank 136, which comprises a top plate 136a and a bottom plate 136b. The driver assembly 130 also includes a gear 138 fixedly coupled to the top plate 136a and bottom plate 136b of the rotor by a rotor pin 136c. The gear 138 is positioned concentrically with the drive shaft 132 and the first axis. The pin 136c couples the gear to the rotor such that torque applied to the gear 138 rotates the rotor 136, and therefore the roller 134. The drive shaft 132 is concentrically coupled to a first bearing 137 to rotate about a first axis. Similarly, the roller 134 comprises a bearing concentrically coupled to a roller bearing pin 133 to rotate about a second axis.

Because it is desired that the entire micropump assembly 110 is sized and shaped to be implanted into a patient (e.g., inside the ocular cavity), the components of the driver assembly 130 can be low-profile. For example, in some embodiments, the ball bearings of the drive shaft 132 and the roller 134 have a diameter of less than 1 mm. In some embodiments, the ball bearings have an outer diameter of between 1.5 mm and 3 mm.

Figure 8:
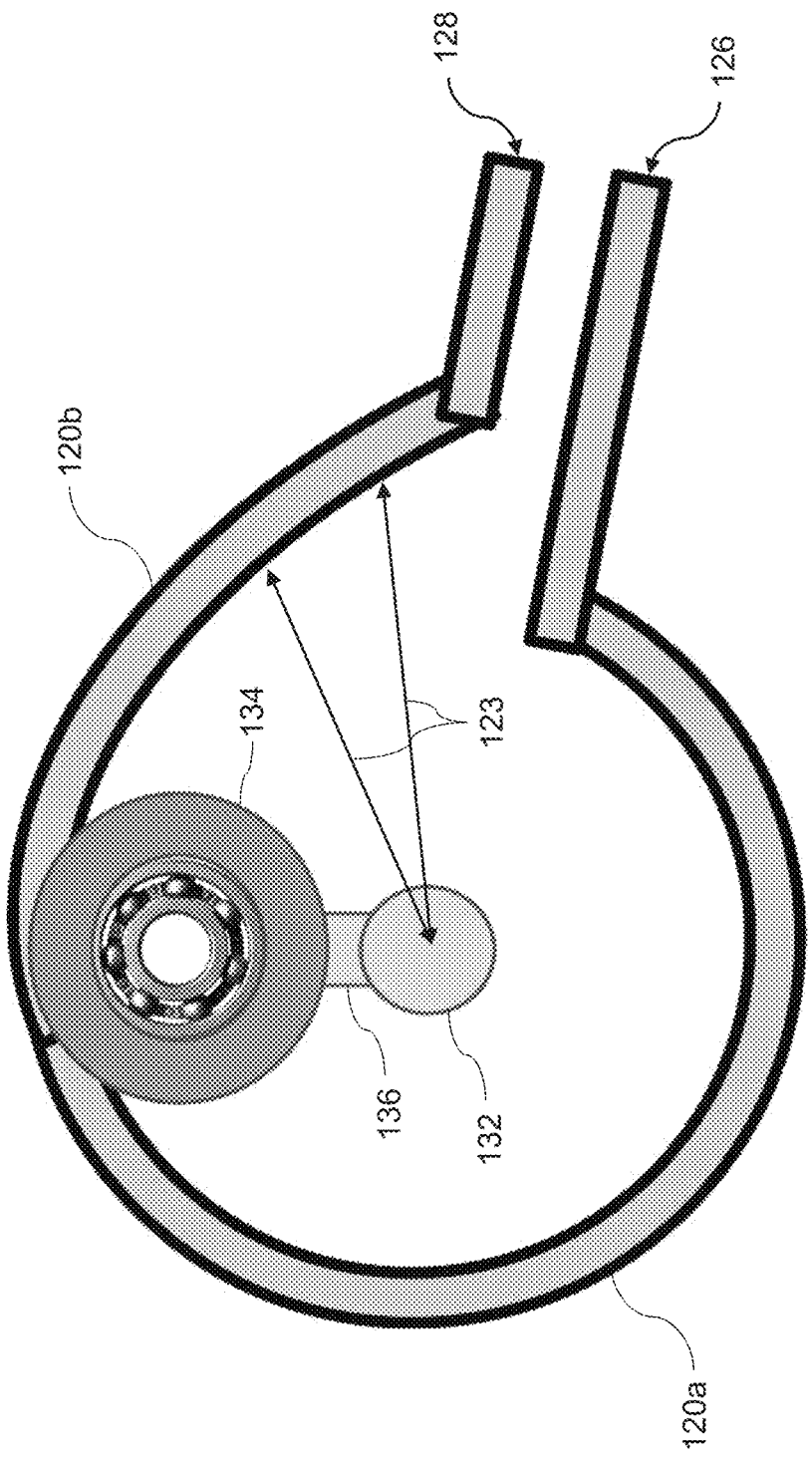
FIG. 8 is a diagrammatic schematic view of a driver circuit and fluid chamber of a micropump assembly, according to an embodiment of the present disclosure.

FIG. 8 is a top view of a driver assembly and a fluid chamber 120, according to one embodiment of the present disclosure. The driver assembly 130 of FIG. 8 may include similar or identical components as the assembly 130 shown in FIGS. 2 and 3, such as a drive shaft 132, a crank 136, and a roller 134. The fluid chamber 120 includes a circular portion 120a and a non-circular portion or spiral portion 120b. In that regard, the non-circular portion 120b is shaped and arranged such that a radius 123 between the drive shaft 132 and the fluid chamber increases in a clockwise direction of the fluid chamber 120. Thus, with the configuration shown in FIG. 8, the micropump assembly 110 can function as a pump over the circular portion 120a, and as a flow controller for the rest of the cycle over the non-circular portion 120b. In that regard, as the roller 134 passes over the circular portion 120a, the fluid chamber 120 is fully compressed, but when the roller 134 passes over the non-circular portion 120b, the fluid chamber 120 is only partially compressed, thereby reducing the hydraulic resistance as the roller 134 rotates clockwise over the non-circular portion 120b. When a positive pressure gradient exists across the micropump 110 (e.g., when the TOP is relatively high), fluid may flow from the inlet 126 to the outlet 128 even without pumping. In this case, pumping is mainly used for clearing and preventing clogs. When a stepper motor is used as the actuator or motor 114, the motor 114 can be controlled to stop at any desired angular location. Thus, the stepper motor 114 can control the roller 134 to stop at a desired position along the non-circular portion 120b. Because the compression of the fluid chamber 120 by the roller 134 gradually decreases as the roller 134 moves clockwise along the non-circular portion 120b, the micropump 110 can act as a variable flow controller to adjust the flow of fluid through the micropump 110 that is caused by the positive pressure gradient. For example, if the motor 114 stops the roller 134 over the circular portion 120a, the fluid chamber 120 is fully compressed such that flow through the fluid chamber 120 is effectively zero. By contrast, when the roller 134 is moved to a location along the non-circular portion 120b that is near the outlet 128, the fluid chamber 120 may not be compressed at all, or only minimally compressed, such that fluid flow through the chamber 120 is effectively unrestricted. The motor 114 can also control the roller 134 to stop at a desired location along the non-circular portion 120b corresponding to a desired amount of compression of the fluid chamber 120, and therefore adjusting the flow of fluid through the chamber 120 to a desired amount.

Figure 9:
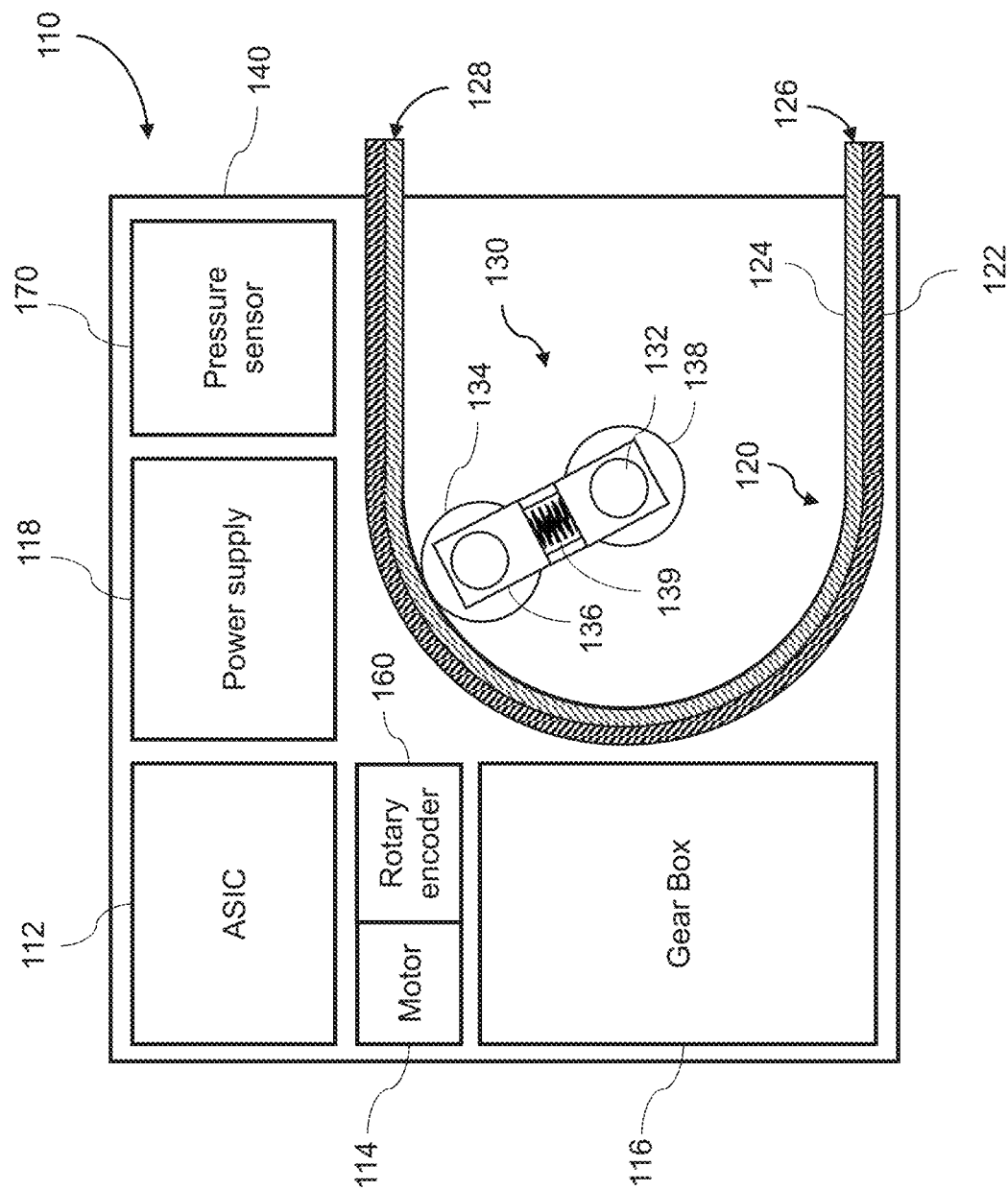
FIG. 9 is a diagrammatic schematic view of a micropump assembly, according to an embodiment of the present disclosure.

FIG. 9 is a diagrammatic schematic view of a micropump assembly 110, according to another embodiment of the present disclosure. The micropump assembly 110 embodiment shown in FIG. 9 can include similar or identical components as the embodiment shown in FIG. 2. For example, the embodiment shown in FIG. 9 includes an ASIC 112, a motor 114, a gear box 116, a power circuit 118, a fluid chamber 120, and a driver assembly 130. Additionally, the micropump assembly 110 includes a rotary encoder 160 in communication with the motor 114, a pressure sensor 170, and a rotor spring 139. The rotary encoder 160 is communicatively coupled to the motor 114 and configured to provide an indication or feedback to indicate the rotational position of the motor 114 to the ASIC 112 and/or motor 114. The rotary encoder 160 can be used to control pumping of fluid through the micropump 110 with volumetric precision. For example, in some embodiments, the micropump assembly 110 can be used to deliver pharmaceutical agents to the patient. The rotary encoder 160 can be used to provide feedback to the ASIC 112 to control dosing of the pharmaceutical with nanoliter precision.

The pressure sensor 170 measures a pressure or pressure gradient across the micropump assembly 120. The pressure sensor 170 is communicatively coupled to the inlet 126 of the fluid chamber 120 to measure a fluid pressure from a source, such as the IOP of the patient's eye 55. The pressure sensor 170 provides signals to the ASIC 112 representative of a measured fluid pressure. The ASIC 112 adjusts performance of the micropump 110 based on the feedback provided by the pressure sensor 170. For example, as IOP fluctuates throughout the day, the ASIC 112 may control the micropump 110 to pump relatively greater volumes of fluid during portions of the day when the IOP measured by the pressure sensor 170 is relatively high. By contrast, the ASIC 112 may control the micropump 110 to pump relatively smaller volumes of fluid, or cease pumping altogether, during portions of the day when the IOP measured by the pressure sensor 170 is relatively low. In this manner the pressure sensor 170 and the ASIC 112 function as a pressure controller. For example, the ASIC 112 can be programmed to maintain the IOP, as measured by the pressure sensor 170, at a desired pressure.

The driver assembly 130 includes a rotor spring 139 positioned between the drive shaft 132 and the roller 134. The spring 139 can be biased to push the roller 134 toward the fluid chamber 120. In that regard, the spring 139 can regulate the force applied by the roller 134 on the membrane 124 of the fluid chamber 120. The spring 139 of the rotor 136 may also exhibit a particular amount of travel, thereby adjusting the radius or distance between the roller and the drive shaft 132. The spring 139 can comprise one or more of a variety of mechanisms to impart a spring force, including compression springs, membranes, magnets, leaf springs, torsion springs, coil springs, or any other suitable type of spring. The spring 139 can provide a number of advantages to the driver assembly 130. For example, the spring 139 may allow the driver assembly 130 to impart a relatively constant compressing force to the membrane 124 of the fluid chamber 120, even as the size and/or shape of the components of the driver assembly 130 vary within tolerances. By maintaining a relatively stable compressing force, it can be ensured that an optimal force is consistently applied to create an effective seal between the membrane 124 and the outer ring 122 of the fluid chamber 120. Accordingly, the longevity of the fluid chamber 120 can be increased because the membrane 124 is not over-stressed. Additionally, maintaining a consistent compressing force can keep friction between the driver assembly 130 and the fluid chamber 120 constant so that the pump consumes less power. Additionally, when residue sticks to an inner surface of the fluid channel 125 within the fluid chamber 120, the spring 139 can prevent jamming because it allows the rotor 136 to retract to pass over the residue.

Figure 10:
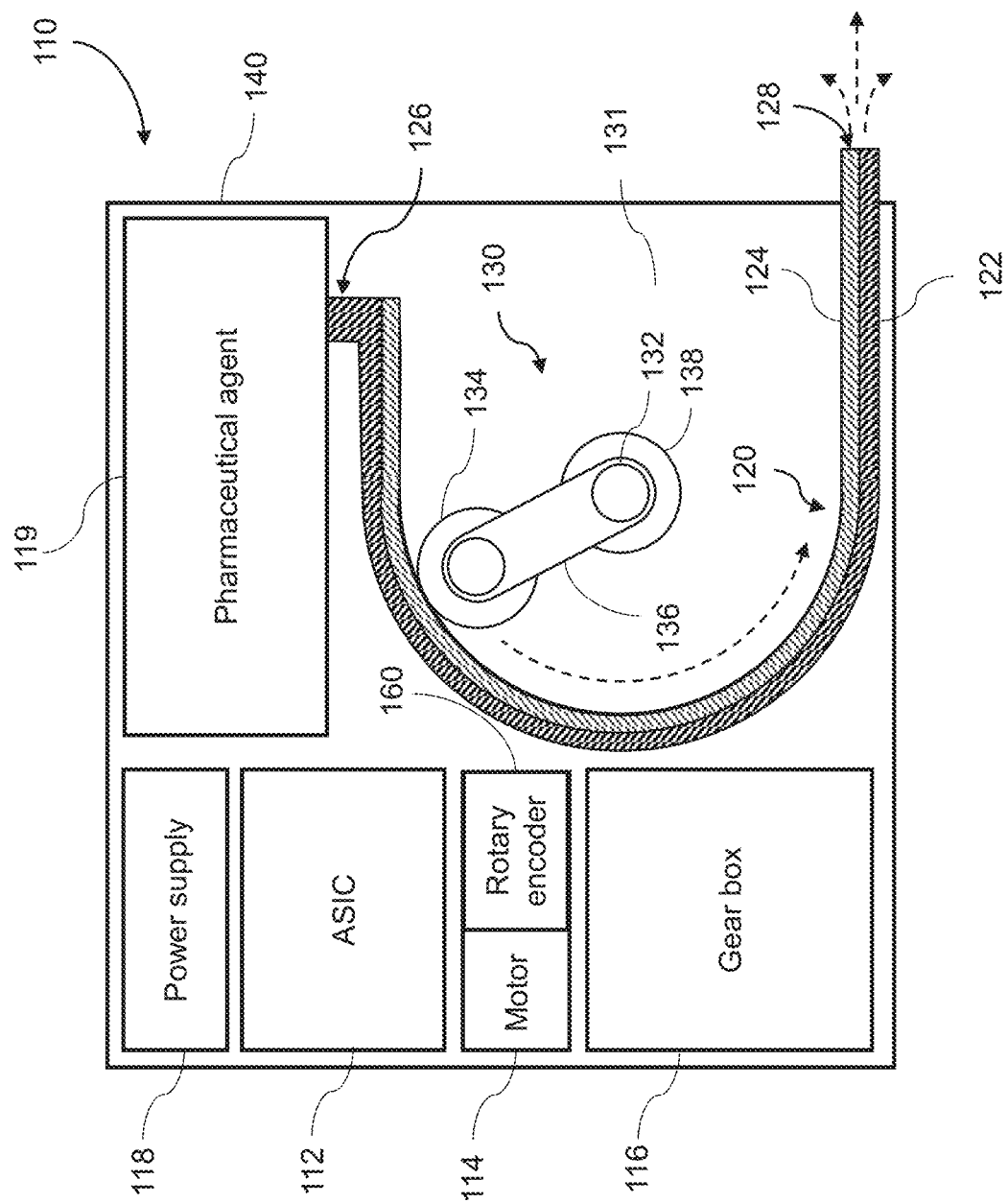
FIG. 10 is a diagrammatic schematic view of a micropump assembly, according to an embodiment of the present disclosure.

FIG. 10 depicts another embodiment of the micropump assembly 110 that is used for delivering a pharmaceutical agents to the patient. The micropump assembly 110 includes a reservoir 119 containing the pharmaceutical agent, with the reservoir 119 in communication with the inlet 126 of the fluid chamber 120. It will be understood that the driver assembly 130 of the embodiment in FIG. 10 is shown rotating in a counter-clockwise fashion toward the outlet 128. The outlet can be connected to or otherwise in fluid communication with an anatomical structure of the patient, such as an organ (e.g., the eye) or a tissue. The micropump assembly 110 shown in FIG. 10 includes a rotary encoder 160 in communication with the ASIC 112 and the motor 114. The rotary encoder 160 can be used as described above to precisely control the volumetric flow of the pharmaceutical agent into the patient via the outlet 128. In some embodiments, the motor 114, rotary encoder 160, and ASIC 112 are configured to enable microdosing of the pharmaceutical agent with nanoliter precision.

Figure 11:
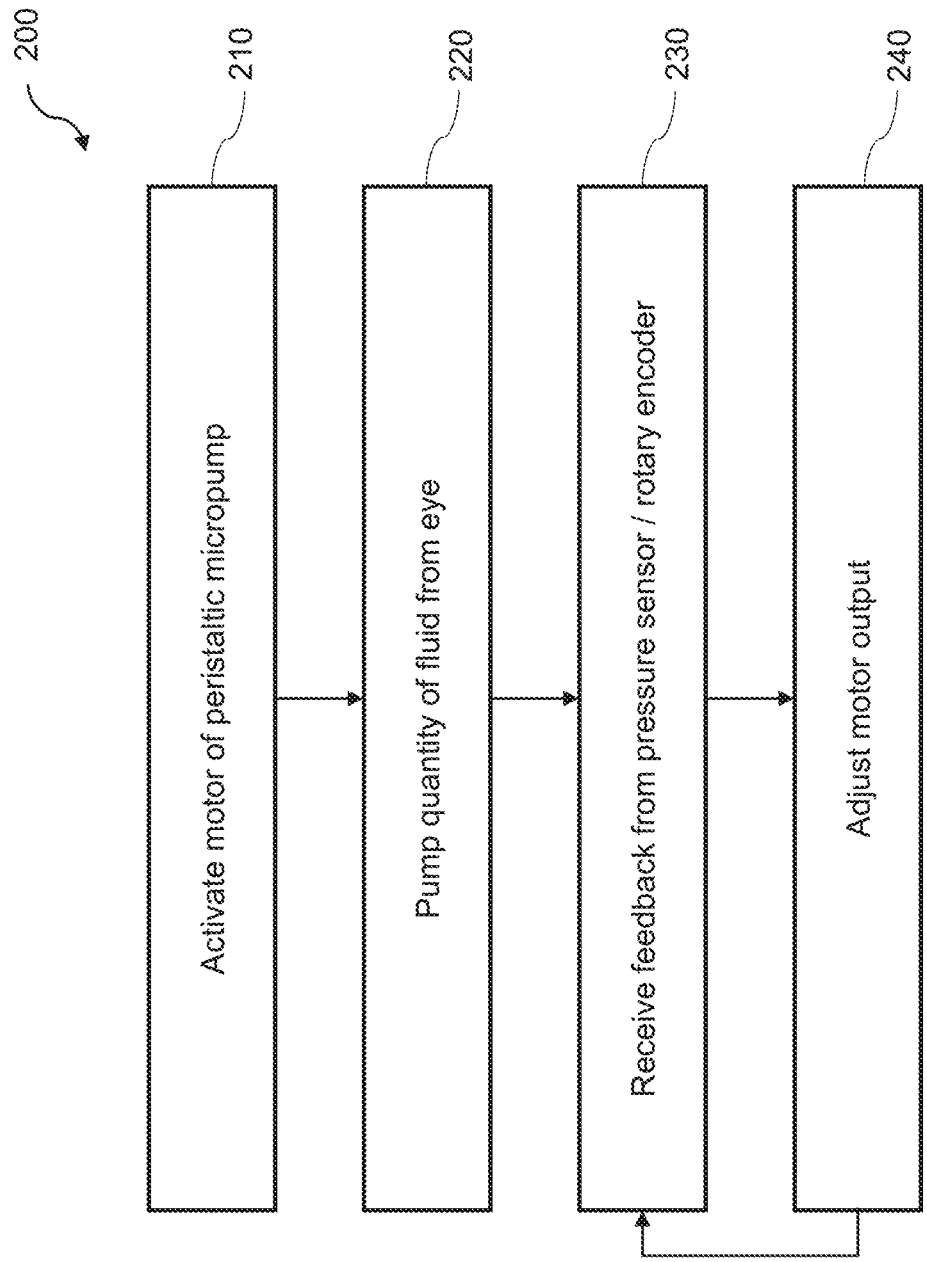
FIG. 11 is a flow chart illustrating a method for pumping fluid from a patient's eye, according to an embodiment of the present disclosure.

FIG. 11 depicts a method 200 of pumping a fluid (e.g., aqueous humor) from a patient's eye in order to reduce and/or regulate the patient's intraocular pressure (IOP). One or more steps of the method described can be carried out by a micropump assembly 110 as described above. In step 210, a motor of a micropump is activated to actuate a pump mechanism comprising a compressing member and a compressible fluid chamber. The motor rotates the compressing member about an axis in a circular motion, with the compressing member compressing a membrane of the fluid chamber against a hard outer ring. The fluid chamber is in communication with the patient's eye such that the micropump displaces fluid from inside the eye to the exterior of the eye. In step 220, the motor continues to rotate to pump a quantity of fluid from inside the eye, thereby reducing the IOP. The micropump may be controlled by an ASIC configured to control the output of the motor. The ASIC may control the output of the motor to displace a predetermined amount of fluid from the eye, to pump fluid at a predetermined flow rate, to operate the motor at a rotational speed, or some combination of these parameters.

In step 230, the ASIC receives feedback from a pressure sensor and/or a rotary encoder, and in step 240, the ASIC adjusts output of the motor based on the received feedback. For example, the feedback from the pressure sensor may include an electrical signal indicating a pressure measurement. The pressure sensor can be in fluid communication with an inlet of the fluid chamber to measure the fluid pressure from a source of the micropump, such as the patient's eye. The ASIC receives the pressure measurement and adjusts motor output according to a protocol. For example, the ASIC may be configured to execute computer instructions to maintain IOP at a particular pressure. When the pressure sensor measures a pressure that exceeds a threshold, the ASIC controls the motor to pump a particular quantity of fluid from the patient's eye. If the pressure measurement falls below a threshold, the ASIC does not activate the motor, or decreases the output of the motor.

In another example, the ASIC executes instructions to deliver an amount of a pharmaceutical agent to the patient. The ASIC activates the motor to rotate and receives feedback signals from the rotary encoder indicating the rotational position of the motor and compressing member. The ASIC controls the motor to rotate until the rotary encoder indicates that the motor is at a predetermined rotational position corresponding to an amount of pharmaceutical agent delivered to the patient.

In another example, the fluid chamber includes a circular portion and a non-circular portion, as described above. When a positive pressure differential is present across the fluid chamber (e.g., when IOP is relatively high), fluid may flow freely through the fluid chamber even without pumping. The motor and compressing member can be used to control the flow rate of fluid by controlling the motor to position the compressing member at a location on the non-circular portion that corresponds to a particular flow rate. To allow fluid to freely flow through the fluid chamber, the ASIC controls the motor to position the compressing member at a location on the non-circular portion at which the fluid chamber is least compressed, or uncompressed. To halt flow of fluid through the fluid chamber, the ASIC controls the motor to position the compressing member at a position along the circular portion of the fluid chamber such that the fluid chamber is fully compressed by the compressing member, thereby restricting flow of fluid through the fluid chamber.

In another example, the ASIC can include instructions to periodically pump fluid through the fluid chamber in order to prevent or remove clogs within the fluid chamber. For example, even when the IOP is below a threshold amount, or when a positive pressure gradient exists across the fluid chamber such that fluid is freely flowing without pumping, the ASIC may periodically activate the motor to compress the fluid chamber along its circumference to dislodge build-up of material and remove clogs.

It will be understood that various modifications can be made to the embodiments described above without departing from the material of the present disclosure. For example, although an ASIC is described as controlling the operation of the micropump assembly, other components and/or circuitry can be used to control operation of the micropump.

For example, the micropump could include analog circuitry configured to control aspects of the micropump. The analog circuitry could function alone, or in combination with one or more microprocessors, field-programmable gate arrays (FPGA's), or any other appropriate analog or digital circuitry. Additionally, aspects of the different embodiments described above can be combined, even if the combinations are not explicitly shown in the drawings. For example, a micropump assembly can include a drug reservoir 119 as in FIG. 10 and a pressure sensor as in FIG. 9, in some embodiments. In another embodiment, a micropump assembly can include a spring-loaded rotor 136 as in FIG. 9 along with the drug reservoir 119 shown in FIG. 10. Additionally, any of the micropump assemblies described above can include a non-circular fluid chamber, as shown in FIG. 8.

The ASIC can include one or more processing components and one or more memory components. The ASIC can be configured to execute computer code according to one or more programming protocols. In some example embodiments, one or more of the ASIC functions described above are executed by a computer program written in, for example, C, C Sharp, C++, Arena, HyperText Markup Language (HTML), Cascading Style Sheets (CSS), JavaScript, Extensible Markup Language (XML), asynchronous JavaScript and XML (Ajax), and/or any combination thereof.

Persons skilled in the art will recognize that the devices, systems, and methods described above can be modified in various ways not explicitly described or suggested above. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A pump assembly, comprising:
    a rotor configured to rotate about an axis and comprising a compressing member at an outer portion of the rotor such that the compressing member is configured to rotate along a circumference;
    a fluid chamber positioned at least partially around the circumference, the fluid chamber comprising:
        a round outer portion comprising an inner face; and,
        a membrane coupled to the round outer portion along a length of the round outer portion such that the membrane opposes the inner face of the round outer portion;
    an actuator configured to cause the rotor to rotate about the axis;
    a processor configured to control an output of the actuator;
    a battery configured to provide electrical power to the processor and the actuator;
    a wireless charging coil coupled to the processor and the battery, the wireless charging coil configured to receive wireless power to recharge the battery; and
    a housing sized and shaped to be implanted in an eye cavity of a patient, wherein the rotor, fluid chamber, actuator, processor, battery, and wireless charging coil are coupled to and contained within the housing,
    wherein the compressing member is configured to deform the membrane of the fluid chamber to compress the fluid chamber against the round outer portion and move a fluid through the fluid chamber.

2. The pump assembly of claim 1, wherein the pump assembly is implantable in a patient for relieving intraocular pressure (IOP).

3. The pump assembly of claim 1, wherein the actuator comprises an electrostatic motor.

4. The pump assembly of claim 1, wherein the rotor comprises a gear concentric with the axis, and wherein the actuator is configured to cause the rotor to rotate about the axis via the gear.

5. The pump assembly of claim 1, wherein the fluid chamber is positioned around the axis in a non-circular pattern.

6. The pump assembly of claim 1, wherein the round outer portion comprises a hard ring and the membrane comprises an elastomeric material.

7. The pump assembly of claim 6, wherein the hard ring comprises a first groove on one side and a second groove on an opposing side, and wherein the membrane is joined to the hard ring using the first groove and the second groove.

8. The pump assembly of claim 6, wherein the hard ring includes at least one of a flat surface or a concave inner surface, and wherein the membrane comprises a thin wall tube comprising a soft rubber material.

9. The pump assembly of claim 6, wherein the hard ring and the membrane are attached by at least one of an adhesive or a weld.

10. A peristaltic pump implantable in a patient for relieving intraocular pressure (IOP), comprising:
    an actuator;
    a drive shaft coupled to the actuator and configured to rotate about a first axis;
    a roller coupled to and radially extending from the drive shaft such that the actuator, via the drive shaft, is configured to rotate the roller about the first axis and along a circumference; and
    a fluid chamber disposed around a portion of the circumference, the fluid chamber comprising:
        a hard outer ring comprising an inner face; and,
        a flexible inner ring comprising a membrane, the flexible inner ring coupled to the outer ring along a length of the outer ring such that the membrane is positioned over an inner surface of the outer ring; and,
    a processor configured to control an output of the actuator;
    a battery configured to provide electrical power to the processor and the actuator;
    a wireless charging coil coupled to the processor and the battery, the wireless charging coil configured to receive wireless power to recharge the battery; and
    a housing sized and shaped to be implanted in an eye cavity of a patient, wherein the actuator, drive shaft, roller, fluid chamber, processor, battery, and wireless charging coil are coupled to and contained within the housing,
    wherein the roller is configured to deform the inner ring of the fluid chamber against the outer ring to compress the fluid chamber and move a fluid through the fluid chamber.

11. The peristaltic pump of claim 10, wherein the outer ring comprises a first groove on one side and a second groove on an opposing side, wherein the membrane is joined to the outer ring using the first groove and the second groove, wherein the membrane comprises a first ridge portion and a second ridge portion, wherein the first ridge portion resides in the first groove, and wherein the second ridge portion resides in the second groove.

12. The peristaltic pump of claim 10, wherein the drive shaft is rotatably coupled to the roller via a first ball bearing, wherein the roller comprises a second ball bearing, and wherein the roller is configured to rotate about a second axis of the ball bearing.

13. The peristaltic pump of claim 10, further comprising a gear assembly coupled to the actuator and the drive shaft, wherein the gear assembly is configured to convert a torque provided by the actuator to the drive shaft.

14. The peristaltic pump of claim 10, further comprising a rotary encoder configured to indicate a rotational position of the roller, wherein the processor comprises an application specific integrated circuit (ASIC) configured to activate the actuator, and wherein the ASIC is configured to control rotation of the roller by the actuator based on the rotational position provided by the encoder.

15. The peristaltic pump of claim 10, wherein the fluid chamber comprises a circular section and a non-circular section, wherein the non-circular section is positioned with respect to the first axis such that a radius between the first axis and the non-circular section of the fluid chamber increases in a direction of the circumference.

\* \* \* \* \*